United States Patent [19]
Audeh et al.

[11] Patent Number: 5,461,181
[45] Date of Patent: Oct. 24, 1995

[54] HETEROGENEOUS CATALYTIC OLIGOMERIZATION OF NORBORNENE

[75] Inventors: Costandi A. Audeh, Princeton, N.J.; James R. Boulton, Chalfont, Pa.; Ross A. Kremer, Ringoes, N.J.; Yusheng Xiong, Newtown, Pa.

[73] Assignee: Mobil Oil Corporation, Fairfax, Va.

[21] Appl. No.: 239,190

[22] Filed: May 5, 1994

[51] Int. Cl.$^6$ ................... C07C 2/02; C07C 2/50
[52] U.S. Cl. ............ 585/533; 585/362; 585/510; 585/520
[58] Field of Search ............ 585/533, 362, 585/510, 520, 361

[56] References Cited

U.S. PATENT DOCUMENTS

| | | | |
|---|---|---|---|
| 4,110,409 | 8/1978 | Myers et al. | 585/361 |
| 4,190,611 | 2/1980 | Lyons et al. | 585/361 |
| 4,416,710 | 11/1983 | Anderson | 149/19.91 |

OTHER PUBLICATIONS

Salomen, R. G. & Kochi, J. K., Tetrahedron Letters No. 27,2529, 1973.
Arnold, D. R., Trecker, D. J., and Whipple, E. B., JACS, 87, 2596, 1965.
Laverty, D. T., McKervey, M. A., Rooney, J. J., and Stewert, A. JCSCC 1368, 1976.
Ito, M., Ishii, Y., Hamanaka, S., and Ogawa, M., Sekiyu Gakkaishi (3), 246, 1986.

*Primary Examiner*—P. Achutamurthy
*Attorney, Agent, or Firm*—Alexander J. McKillop; Dennis P. Santini; Robert B. Furr, Jr.

[57] ABSTRACT

A process for the heterogeneous catalytic oligomerization of norbornene comprising the steps of reacting norborene in the presence of a solid catalyst comprising a porous crystalline material having a Constraint Index of from about 0.1 to about 12 under oligomerization conditions to evolve a product containing norbornene oligomers.

9 Claims, No Drawings

HETEROGENEOUS CATALYTIC OLIGOMERIZATION OF NORBORNENE

FIELD OF THE INVENTION

This invention relates a method for oligomerizing norbornene to form an oligomerate which is useful as a high density fuel. The invention further provides a high density fuel comprising norbornene oligomers.

BACKGROUND OF THE INVENTION

Synthesis of neat norbornene oligomers (primarily dimers) via homogeneous catalysis is described in the technical literature. While it would be desirable to convert norbornene into a mixture of dimers and trimers useful as a high-energy, liquid fuel, no reference of which the Applicants are aware discloses either a commcerially useful process for upgrading norbornene to a suitable mixture of norbornene dimers and trimers over a heterogeneous catalyst. Moreover, no reference of which the Applicants are aware teaches a mixture of norbornene dimers and trimers having properties appropriate for a high energy-density liquid fuel.

U.S. Pat. No. 4,416,710 to Anderson discloses missile fuel compositions using polynorbornene as a binder for liquid and solid materials.

U.S. Pat. No. 4,190,611 to Lyons et al. describes preparation of high-energy fuels by co-oligomerization of norbornene and norbornadiene using a complex three-component homogeneous catalyst (cobaltic or cobaltous acetylacetonate, 1,2-bisdiphenylphosphino ethane and an alkyl aluminum chloride).

A brief summary of several pertinent literature references describing oligomerization of norbornene with homogeneous catalysts is given below.

Photodimerization of norbornene is described by Salomen and Kochi (Salomen, R. G. & Kochi, J. K. *Tetrahedron Letters* No. 27, 2529, 1973) and by Arnold et al. (Arnold, D. R., Trecker, D. J., and Whipple, E. B., JACS, 2596, 1965). Salomen and Kochi achieved an 88% yield of almost pure exo-trans-exo norbornene dimer by irradiating a solution of norbornene in THF containing a copper triflate catalyst for six days. The product, however, was a solid with a melting point of +63.5°–64.0° C. and, thus, not suitable as a high-energy fuel.

Arnold et al. achieved a 26% yield of almost pure exo-trans-exo norbornene dimer by irradiating norbornene in an anhydrous ether solvent using cuprous bromide catalyst for 149 hours. The isolated exo-trans-exo norbornene dimer was a solid with a melting point of +64°–65° C. and, thus, was also not suitable as a high-energy fuel.

Arnold et al. also achieved a 23% yield of primarily endo-trans-exo norbornene dimer by irradiating norbornene in a benzene solvent for 192 hours. The isolated dimer product was also a solid having a melting point of +38.5°–39.5° C., and, thus, not suitable as a high-energy fuel.

Laverty et al. (Laverty, D. T., McKervey, M. A., Rooney, J. J., and Stewert, A., *JCSCC* 1368, 1976) produced a mixture of four different norbornene dimers (trans-anti, cis-anti, cis-syn, and trans-syn bi-2,2-norbornyldiene) by reacting norbornene in dry carbon sulfide or benzene solvents using soluble $WCl_6$ or $ReCl_3$ catalysts. The product also contained chlorinated derivatives which are incompatible with high-energy fuel applications.

Finally, Ito et al. (Ito, M., Ishii, Y., Hamanaka, S., and Ogawa, M., *Sekiyu Gakkaishi* (3), 246, 1986) achieved a 59.7% yield of almost exclusively a single norbornene dimer (trans-anti bi-2,2-norbornylidene) by reacting norbornene for six hours at 120° C. in an ethanol solvent in a sealed glass tube using a nickel complex catalyst ($Ni_2Cl_2(Ph_3P)_2$ and $NaBH_4$). No information is given on isolation and characterization of the properties of this dimer.

Thus it would be desirable to provide a process which selectively dimerizes norbornene over a heterogeneous catalyst to provide a product useful as a high density fuel.

SUMMARY OF THE INVENTION

This invention comprises a process for the catalytic oligomerization of norbornene which comprises reacting norbornene in the presence of a heterogeneous catalyst comprising a synthetic crystalline material having a Constraint Index of from about 0.1 to about 12, under catalytic oligomerization conditions to produce norbornene oligomers. In a preferred embodiment, the process of this invention principally produces dimers and trimers of norbornene.

The process of this invention may be operated in batch or continuous mode. If the process is operated in the continuous mode, the weight hourly space velocity (based upon catalyst) is preferably controlled within the ranges set forth below to provide a per-pass conversion of at least about 70 weight percent of the norbornene feed, preferably at least about 80 weight percent, and more preferably at least about 90 weight percent. The product stream contains both dimers and trimers of norbornene, typically in dimer:trimer molar ratios of from about 1:1 to about 6:1, and preferably within the range of from about 2:1 to about 4:1. The process of the invention typically produces approximately equimolar concentrations of four norbornene dimers: trans-anti, cis-anti, cis-syn and trans-syn bi-2,2-norbornylidene.

The crystalline materials useful as catalyst components in the present process have an effective pore size of generally from about 5 to about 8 Angstroms, such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although, in some instances, excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of the particular zeolite solely from theoretical structural considerations.

A convenient measure of the extent to which a zeolite provides control to molecules of varying sizes to its internal structure is the Constraint Index of the zeolite. The method by which the Constraint Index is determined is described in U.S. Pat. No. 4,016,218, incorporated herein by reference for details of the method. U.S. Pat. No. 4,696,732 discloses Constraint Index values for typical zeolite materials and is incorporated by reference as if set forth at length herein.

In a preferred embodiment, the catalyst is a zeolite having a Constraint Index of between about 0.1 and about 12. Examples of such zeolite catalysts include ZSM-4, ZSM-5, ZSM-11, ZSM-12, ZSM-22, ZSM-23, ZSM-35, ZSM-48, as well as MCM-22, PSH-3, SSZ-25, and zeolite Beta.

Zeolite ZSM-5 and the conventional preparation thereof are described in U.S. Pat. No. 3,702,886, the disclosure of which is incorporated herein by reference. Other preparations for ZSM-5 are described in U.S. Pat. Nos. Re. 29,948 (highly siliceous ZSM-5); 4,100,262 and 4,139,600, the disclosure of these is incorporated herein by reference. Zeolite ZSM-11 and the conventional preparation thereof are described in U.S. Pat. No. 3,709,979, the disclosure of which is incorporated herein by reference. Zeolite ZSM-12 and the conventional preparation thereof are described in U.S. Pat. No. 3,832,449, the disclosure of which is incorporated herein by reference. Zeolite ZSM-23 and the conventional preparation thereof are described in U.S. Pat. No. 4,076,842, the disclosure of which is incorporated herein by reference. Zeolite ZSM-35 and the conventional preparation thereof are described in U.S. Pat. No. 4,016,245, the disclosure of which is incorporated herein by reference. Another preparation of ZSM-35 is described in U.S. Pat. No. 4,107,195, the disclosure of which is incorporated herein by reference. ZSM-48 and the conventional preparation thereof is taught by U.S. Pat. No. 4,375,573, the disclosure of which is incorporated herein by reference.

Gallium-containing catalysts may be used in the present invention and are disclosed in U.S. Pat. No. 4,350,835 and U.S. Pat. No. 4,686,312, both of which are incorporated by reference as if set forth at length herein.

Zinc-containing catalysts may be used in the present invention, for example, U.S. Pat. No. 4,392,989 and U.S. Pat. No. 4,472,535, both of which are incorporated by reference as if set forth at length herein.

Catalysts such as ZSM-5 combined with a Group VIII metal described in U.S. Pat. No. 3,856,872, incorporated by reference as if set forth at length herein, are also useful in the present invention.

Synthetic porous crystalline materials useful in the present invention include the PSH-3 composition of U.S. Pat. No. 4,439,409, the SSZ-25 composition of U.S. Pat. Nos. 4,665,110 and 4,826,667, and the MCM-22 composition of U.S. Pat. 4,954,325. MCM-22 is also described in U.S. Pat. Nos. 4,992,615, 5,012,033, and 5,073,665.

The synthetic porous crystalline material, or zeolite, catalyst preferred for use in the process of this invention, referred to herein as "zeolite MCM-22" or simply "MCM-22", appears to be related to the composition named "PSH-3" described in U.S. Pat. No. 4,439,409. Zeolite MCM-22 does not appear to contain all the components apparently present in the PSH-3 compositions and is not contaminated with other crystal structures such as ZSM-12 or ZSM-5. Moreover, zeolite MCM-22 exhibits unusual sorption capacities and unique catalytic utility when compared to the PSH-3 compositions synthesized in accordance with U.S. Pat. No. 4,439,409.

| Heterogeneous Catalytic Norbornene Oligomerization Conversion Conditions | | | |
|---|---|---|---|
| | Useful | Typical | Preferred |
| Temperature, | 75 to 250 | 75 to 200 | 100 to 175 |
| °C. | | | |
| Pressure, psig | 0–1000 | 0–500 | 0–250 |
| WHSV, hr.$^{-1}$ | 0.05 to 10 | 0.05 to 5 | 0.1 to 0.3 |

EXAMPLES

The following three examples describe our preparation of norbornene oligomers via simple liquid-phase oligomerization of norbornene using heterogeneous zeolite catalysts. It is important to note for comparison, when considering the products of these examples as high-energy fuels, that the net heat of combustion of current military rocket fuel—JP-10 (exo-tetrahydrodicyclopentadiene)— is 141,800 BUT/gallon.

Example 1

1000 gms of neat norbornene (99% purity) were charged to a five-liter glass reactor together with 61 gms of ZSM-5 zeolite extrudate catalyst. The reactor was blanketed with nitrogen, agitated with a magnetic stirrer, heated to reflux temperature at ambient pressure and allowed to react for 21.6 hours. The reactor was then cooled to room temperature and the product recovered. Analysis by capillary gas chromotography showed 80.7% conversion to norbornene oligomers (>95% dimers and trimers) with a weight ratio of dimers/trimers of 3.8/1. NMR analysis showed that the norbornene dimer fraction consisted of approximately equal concentrations of four norbornene dimers, trans-anti, cis-anti, cis-syn and trans-syn bi-2,2-norbornylidene. The unreacted norbornene was separated from the reaction product via distillation and saved for recycling to the next reaction. The mixed norbornene oligomer product after removal of the unreacted norbornene was a low-viscosity liquid having a specific gravity of 1.001, a pour point of −50° F. and a net heat of combustion of 149,884 BTU/gallon.

Example 2

1000 gm of neat norbornene (99% purity) were charged to an agitated one-gallon stainless steel autoclave together with 70 gms of ZSM-23 zeolite extrudate catalyst. The reactor was blanketed with nitrogen, heated, and the oligomerization carried out according to the following schedule—6.3 hours at 150° C., 1.2 hours at 160° C. and 19.1 hours at 175° C. The reactor was then cooled to room temperature and the product recovered. Analysis by capillary gas chromotography showed 85.8% conversion of norbornene to norbornene oligomers (>90% dimers and trimers) with a weight ratio of dimers/trimers of 2.9/1. NMR analysis showed that the norbornene dimer fraction consisted of approximately equal concentrations of four norbornene dimers—trans-anti, cis-anti, cis-syn and trans-syn bi-2,2-norbornylidene. The unreacted norbornene was separated from the reaction product via distillation and saved for recycling to the next reaction. The mixed norbornene oligomer product, after removal of the unreacted norbornene, was a low-viscosity liquid having a specific gravity of 1.014, a pour point of −30° F. and a net heat of combustion of 150,707 BTU/gallon.

Example 3

240 gms of norbornene (99% purity) were charged to a 500 cc agitated stainless steel autoclave together with 15 gms of zeolite beta extrudate catalyst and 60 gms of heptane solvent. The reactor was blanketed with nitrogen, heated, and the oligomerization carried out for 25.9 hours at 150° C. and 21.3 hours at 175° C. The reactor was then cooled to room temperature and the product recovered. Analysis by capillary gas chromotography showed 87.3% conversion to norbornene oligomers (>90% dimers and trimers) with a weight ratio of dimers/trimers of 2.4/1.

Changes and modifications in the specifically described embodiments can be carried out without departing from the scope of the invention which is intended to be limited only by the scope of the appended claims.

What is claimed is:

1. A process for the heterogeneous catalytic oligomerization of norbornene comprising the steps of reacting norborene in the presence of a solid catalyst comprising a porous crystalline material having the structure of at least one selected from the group consisting of ZSM-4, ZSM-5, ZSM-11, ZSM-12, ZSM-22, ZSM-23, ZSM-35, ZSM-48, MCM-22, PSH-3, SSZ-25, and zeolite beta under oligomerization conditions to evolve a product containing norbornene oligomers.

2. The process of claim 1 wherein said product is enriched in norbornene dimers and trimers.

3. The process of claim 1 wherein said oligomerization conditions comprise temperature of from about 75° to about 250° C., pressure of from about 0 to about 1000 psig, and weight hourly space velocity of from about 0.05 to about 10 hr.$^{-1}$.

4. The process of claim 3 wherein said oligomerization conditions further comprise temperature of from about 75° to 200° C., pressure of from about 0 to about 500 psig, and weight hourly space velocity of from about 0.05 to about 5 hr.$^{-1}$.

5. The process of claim 4 wherein said oligomerization conditions further comprise temperature of from about 100° to about 175° C., pressure of from about 0 to about 250 psig, and weight hourly space velocity of from about 0.1 to about 0.3 hr.$^{-1}$.

6. A continuous process for converting norbornene into a mixture of norbornene dimers and trimers comprising the steps of converting norbornene in the presence of a solid catalyst comprising porous crystalline material having the structure of at least one selected from the group consisting of ZSM-4, ZSM-5, ZSM-11, ZSM-12, ZSM-22, ZSM-23, ZSM-35, ZSM-48, MCM-22, PSH-3, SSZ-25, and zeolite beta under oligomerization conditions at a per-pass conversion of at least about 70 weight percent based upon the norbornene feed to evolve a product containing norbornene dimers and trimers in a dimer:trimer molar ratio of from about 1:1 to about 6:1.

7. The process of claim 6 further comprising continuously converting norbornene to a mixture of norbornene dimers and trimers at a per-pass norbornene conversion of at least about 80 weight percent.

8. The process of claim 7 further comprising continuously converting norbornene to a mixture of norbornene dimers and trimers at a per-pass norbornene conversion of at least about 90 weight percent.

9. The process of claim 8 further comprising continuously converting norbornene to a mixture containing norbornene dimers in a dimer:trimer molar ratio of from about 2:1 to about 4:1.

* * * * *